United States Patent [19]

Stokes

[11] Patent Number: 5,325,869
[45] Date of Patent: Jul. 5, 1994

[54] APPARATUS FOR LOAD AND DISPLACEMENT SENSING

[76] Inventor: Theodore J. Stokes, 512 W. 5th St., Monroe, Mich. 48161

[21] Appl. No.: 808,105

[22] Filed: Dec. 16, 1991

[51] Int. Cl.$^5$ .............................................. A61B 5/103
[52] U.S. Cl. .................................... 128/779; 128/782; 73/172; 73/862.046
[58] Field of Search ..................... 128/779, 782, 774; 73/767, 768, 779, 841, 862.041, 862.042, 862.043, 862.046, 862.69, 172, DIG. 3; 338/32 H; 177/DIG. 5

[56] References Cited

U.S. PATENT DOCUMENTS

| | | | |
|---|---|---|---|
| 3,974,491 | 8/1976 | Sipe | 340/573 |
| 4,426,884 | 1/1984 | Polchaninoff | 73/172 |
| 4,503,705 | 3/1985 | Polchaninoff | 73/172 |
| 4,561,314 | 12/1985 | Alley et al. | 73/862.69 |
| 4,612,502 | 9/1986 | Spies | 324/208 |
| 4,647,918 | 3/1987 | Goforth | 340/573 |
| 4,731,579 | 3/1988 | Petersen et al. | 324/207 |
| 4,738,325 | 4/1988 | Bullivant et al. | 177/210 EM |
| 4,745,811 | 5/1988 | Gray | 73/708 |
| 4,745,930 | 5/1988 | Confer | 128/779 |
| 4,813,436 | 3/1989 | Au | 128/779 |
| 4,862,743 | 9/1986 | Seitz | 73/172 |
| 4,866,854 | 9/1989 | Seltzer | 33/558 |
| 5,055,820 | 10/1991 | Kimura et al. | 338/32 H |
| 5,070,737 | 12/1991 | Reilly | 73/862.04 |
| 5,107,854 | 4/1992 | Knotts et al. | 128/779 |

FOREIGN PATENT DOCUMENTS

| | | | |
|---|---|---|---|
| 237054 | 7/1986 | Fed. Rep. of Germany | 128/779 |
| 558183 | 5/1977 | U.S.S.R. | 73/862.69 |

*Primary Examiner*—Stephen C. Pellegrino
*Assistant Examiner*—Guy V. Tucker
*Attorney, Agent, or Firm*—Brooks & Kushman

[57] ABSTRACT

An apparatus for load and displacement sensing adapted for measuring normal and shear forces exerted on load bearing portions of a body. The apparatus includes a deformable pad and a plurality of sensors. Each sensor includes at least one magnet and at least one Hall-effect transducer affixed to opposite sides of the deformable pad. Normal forces are measured utilizing magnets having a planar North and South polarizations and the magnitude and direction of shear forces are measured utilizing magnets having alternating North and South pole segments disposed longitudinally therewithin. In another embodiment, normal and shear forces are measured utilizing a magnet having a point-magnetization. The force exerted on the body deforms the pad, bringing the magnet in close proximity to the transducer, which senses the change in the magnetic flux density.

1 Claim, 12 Drawing Sheets

APPARATUS FOR LOAD AND DISPLACEMENT SENSING

TECHNICAL FIELD

The present invention is related to a sensor and an apparatus, adapted for use as a shoe insert, for load and displacement sensing.

BACKGROUND ART

As is known, there are a number of load sensing devices useful for measuring forces exerted on a body. For example, U.S. Pat. No. 4,738,325, issued to Bullivant, et al., discloses a Hall-effect weight transducer. The transducer senses changes in the magnetic field generated by a pair of magnets affixed to a housing. The field change is due to the relative movement of the upper and lower inner surfaces of the housing from the application of a weight to the housing.

U.S. Pat. No. 4,745,811, issued to Gray, discloses a pressure monitoring apparatus. The apparatus utilizes a pressure gauge having Bourdon tube with a pair of magnets affixed thereto. The tube is responsive to external pressure and a hall effect detector mounted in close proximity to the magnets generates a signal proportional to the movement of the magnets.

U.S. Pat. No. 4,866,854, issued to Seltzer, discloses a multi-axis displacement sensor for sensing the movement of two relatively movable parts. The sensor includes at least two magnetic poles mounted on one of the movable parts and two hall effect devices mounted on the other part. A displacement of the parts causes relative movement between the Hall-effect devices and the magnetic poles.

U.S. Pat. No. 3,974,491, issued to Sipe, discloses a device for signaling a patient when a predetermined load is placed on the patient's foot. The signaling device utilizes a resilient foot pad having a liquid filled tube and is controlled by a pressure responsive means in communication with the tube.

U.S. Pat. No. 4,647,918, issued to Goforth, discloses a notification system for monitoring critical pressure points on the feet of persons having diminished sensation of the feet. The systems utilizes a plurality of pressure transducers electrically connected to a microprocessor. An alarm indicates when a predetermined threshold of pressure is exceeded.

U.S. Pat. No. 4,745,930, issued to Confer, discloses a force sensing insole for use with an electro-goniometer for analyzing the gait of a patient. Normally open contact switches positioned in the open chambers of the body member are brought into contact with each other upon a compressive force applied to the insole.

U.S. Pat. No. 4,813,436 discloses a motion analysis system having pressure responsive shoes or insoles worn by the subject. The insoles utilize pressure transducers and provide signals which are processed, whereby a display indicates the pressure applied to the subject's foot while moving.

DISCLOSURE OF INVENTION

It is a general object of the present invention to provide a sensor and an apparatus for load and displacement sensing adapted for measuring the loading exerted upon the load bearing portions of a body.

It is another object of the present invention to provide a sensor and an apparatus for measuring the normal loads exerted on the load bearing portions of the body.

It is a further object of the present invention to provide a sensor and an apparatus for measuring the magnitude and direction of two-dimensional shear forces exerted on the load bearing portions of the body.

It is an additional another object of the present invention to provide a sensor and an apparatus for measuring both normal loads and the magnitude and direction of the shear forces exerted on the load bearing portions of the body.

It is still a further object of the present invention to provide a sensor and an apparatus utilizing tilt compensation for measuring normal loads and for measuring the magnitude and direction of shear forces and exerted on the load bearing portions of the body.

The advantages accruing to the sensor and apparatus of the present invention are numerous. For example, since the sensor utilizes at least one magnet and Hall-effect transducer pair, precise measurements of forces can be made due to the capability of the transducer to sense extremely small fluctuations in the magnetic flux density of the magnet.

In carrying out the above objects and other objects and features of the present invention, an apparatus is provided for load and displacement sensing, adapted for measuring the normal load exerted upon the load bearing portions of a body. The apparatus includes a deformable pad having a first and second side and a plurality of sensors. Each sensor has a magnet affixed to one side of the deformable pad and a transducer for sensing the magnetic field strength affixed to the other side of the deformable pad. Each transducer is aligned with one of the magnets and has an output proportional to the normal load, which deforms the pad and brings the transducers in close proximity to the magnets.

In further carrying out the above objects and other objects and features of the present invention, an apparatus is provided for load and displacement sensing, adapted for measuring the magnitude and direction of two-dimensional shear forces exerted upon the load bearing portions of a body. The apparatus includes a deformable pad having a first and second side and a plurality of sensors. Each sensor has at least two magnets affixed to one side of the deformable pad and at least two transducers for sensing the magnetic field strength affixed to the other side of the deformable pad. Each transducer is aligned with one of the magnets and has an output which varies according to the magnitude and direction of the shear forces, which move the magnets in relation to the transducers.

In still further carrying out the above objects and other objects of the present invention, an apparatus is provided for load and displacement sensing adapted for measuring the magnitude and direction of normal and two-dimensional shear forces exerted upon the load bearing portions of a body. The apparatus includes a deformable pad having a first and second side and a plurality of sensors. Each sensor has at least three magnets affixed to one side of the deformable pad and at least three transducers for sensing the magnetic field strength affixed to the other side of the deformable pad. Each transducer is aligned with one of the magnets and has an output which varies according to the magnitude and direction of the normal and two-dimensional shear forces, which move the magnets in relation to the transducers.

In further carrying out the above objects, an apparatus is provided for load and displacement sensing adapted for measuring the normal and two-dimensional shear forces exerted upon the load bearing portions of a body. The apparatus includes a deformable pad having a first and second side and a plurality of sensors. Each sensor has at least five magnets affixed to one side of the deformable pad and at least five transducers for sensing the magnetic field strength affixed to the other side of the deformable pad. Each transducer is aligned with one of the magnets and has an output which varies as a function of the magnitude and direction of the normal and shear forces, which deform the pad and move the magnets in relation to the transducers.

In still further carrying out the above objects and other objects and features of the present invention, an apparatus is provided for load and displacement sensing adapted for measuring the magnitude and direction of normal and two-dimensional shear forces. The apparatus includes a deformable pad having a first and second side and a plurality of sensors. Each sensor has at least one magnet affixed to one side of the deformable pad, the magnet having a point source magnetization, and at least three transducers for sensing the magnetic flux density. The transducers are affixed to the other side of the deformable pad, each transducer having an output which varies according to the magnitude and direction of the normal and two-dimensional shear forces, the forces deforming the pad and moving the magnet in relation to the transducers.

In still further carrying out the above objects, a sensor is provided for load and displacement sensing adapted for measuring the magnitude and direction of two-dimensional shear forces. The sensor includes a deformable pad having a first and second side and at least two magnets being affixed to one side of the deformable pad. The sensor further includes at least two transducers for sensing the magnetic field strength affixed to the other side of the deformable pad. The magnets have alternating North and South pole segments disposed longitudinally therewithin and each transducer is aligned with one of the magnets and has an output which varies according to the magnitude and direction of the shear forces, which deform the pad and move the magnets in relation to the transducers.

In further carrying out the above objects and other objects of the present invention, a sensor is provided for load and displacement sensing adapted for measuring the magnitude and direction of normal and two-dimensional shear forces. The sensor includes a deformable pad having a first and second side and at least three magnets affixed to one side of the deformable pad. The sensor further includes at least three transducers for sensing the magnetic field strength affixed to the other side of the deformable pad. Each transducer is aligned with one of the magnets and has an output which varies according to the magnitude and direction of the normal and two-dimensional shear forces, which deform the pad and move the magnets in relation to the transducers.

In further carrying out the above objects and other objects and features of the present invention, a sensor is provided for load and displacement sensing adapted for measuring the magnitude and direction of normal and two-dimensional shear forces. The sensor includes a deformable pad having a first and second side and a magnet affixed to one side of said deformable pad, the magnet having a point source magnetization. The sensor also includes at least three transducers for sensing the magnetic flux density, the transducers being affixed to the other side of the deformable pad, each transducer having an output which varies according to the magnitude and direction of the normal and two-dimensional shear forces, the forces deforming the pad and moving the magnet in relation to the transducers.

In still further carrying out the above objects, a sensor is provided for load and displacement sensing adapted for measuring the magnitude and direction of normal and two-dimensional shear forces. The sensor includes a deformable pad having a first and second side and at least five magnets being affixed to one side of the deformable pad. The sensor further includes at least five transducers for sensing the magnetic field strength being affixed to the other side of the deformable pad. Each transducer is aligned with one of the magnets and has an output which varies as a function of the magnitude and direction of the normal and shear forces, which deform the pad and move the magnets in relation to the transducers.

In further carrying out the above objects, a method of load and displacement sensing for measuring the normal forces exerted on the load bearing portions of a body is provided. The method includes providing a deformable pad having a first and second side and providing a plurality of sensors, each sensor having a magnet affixed to one side of said deformable pad and a transducer for sensing the magnetic field strength affixed to the other side of the deformable pad and aligned with one of the magnets. The method further includes applying the normal forces to the body to deform the pad, bringing the transducers in close proximity to the magnets and sensing the magnetic field strength by the transducer and generating an output based on the magnitude of the normal forces.

In still further carrying out the above objects and other objects, a method of load and displacement sensing for measuring the magnitude and direction of two-dimensional shear forces exerted on the load bearing portions of a body is provided. The method includes providing a deformable pad having a first and second side and providing a plurality of sensors, each sensor having at least two magnets affixed to one side of the deformable pad and at least two transducers for sensing the magnetic field strength affixed to the other side of the deformable pad and aligned with the magnets. The method further includes applying the shear forces to the body to deform the pad, moving the magnets in relation to the transducers, sensing the magnetic field strength by the transducer and generating an output based on the magnitude and direction of the shear forces.

The above objects and other objects and features of the invention will be readily appreciated by one of ordinary skill in the art from the following detailed description of the best modes for carrying out the invention when taken in connection with the following drawings.

BEST MODES FOR CARRYING OUT THE INVENTION

Normal Force Sensing

Figure 1:
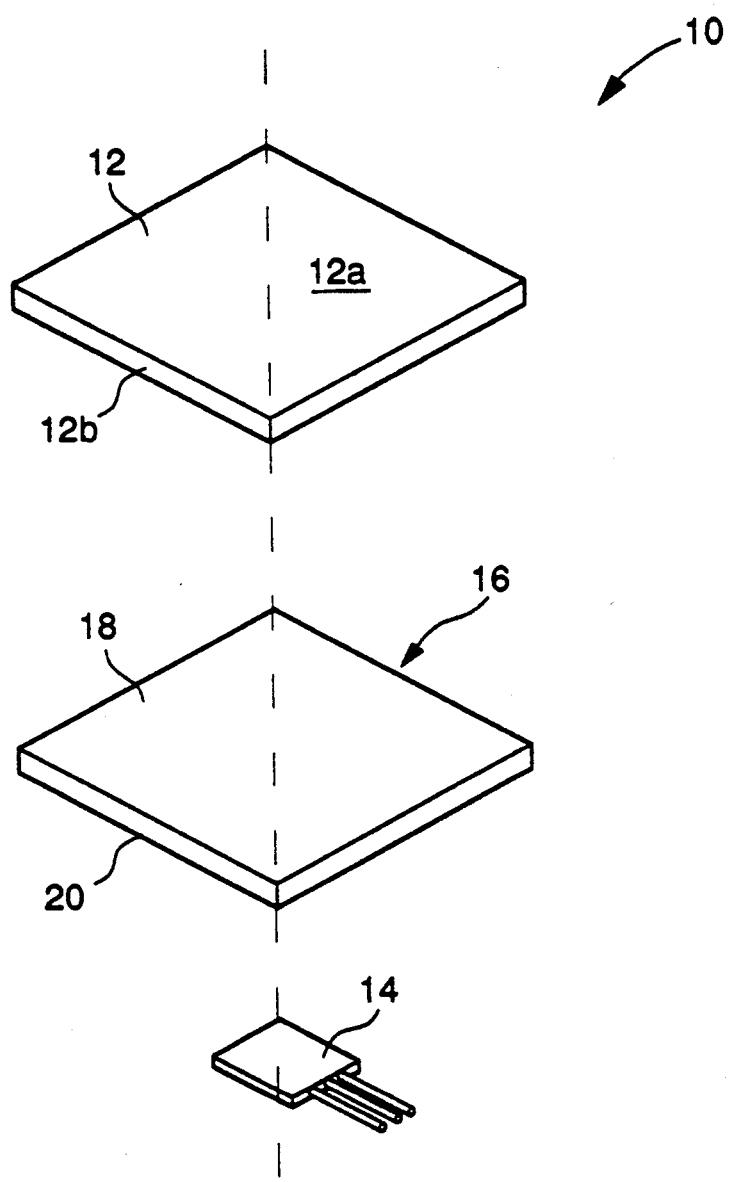
FIG. 1 is an exploded perspective view of the first preferred embodiment of the sensor for measurement of normal forces utilizing a magnet having planar polarizations.
Figure 2:
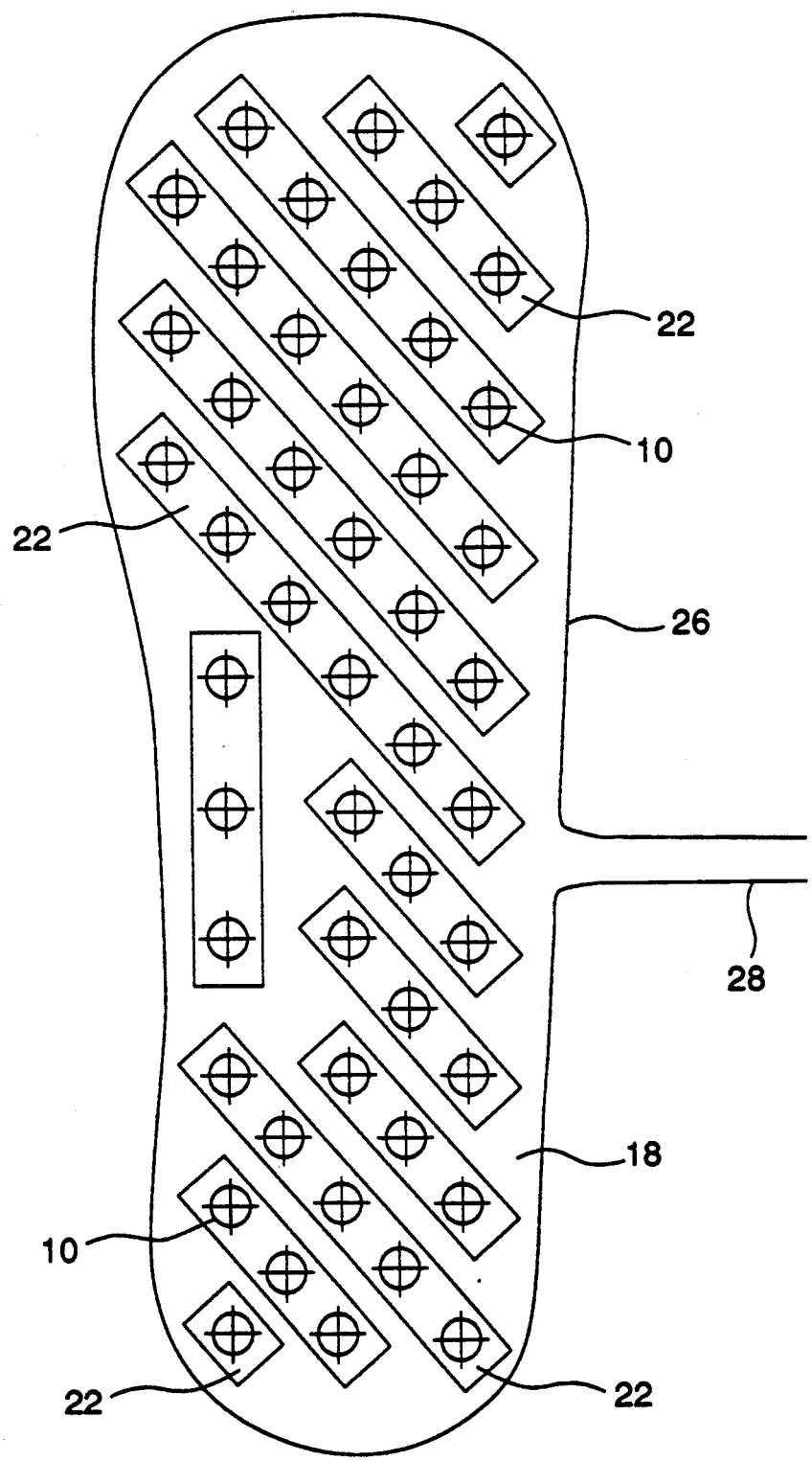
FIG. 2 is an illustration of a deformable pad having a 48-sensor array, in accordance with the present invention.

Referring now to FIGS. 1 and 2, a first embodiment of the load sensing apparatus of the present invention is shown. The first embodiment is useful for measuring normal (i.e. axial) loads and associated displacements and includes a deformable pad 26 and a plurality of sensors 10. Sensor 10 is shown to include a magnet 12 and a Hall-effect transducer 14 and cooperate with deformable square 16, which represents a section of deformable pad 26. Thus, the deformable pad 26 is comprised of a plurality of deformable squares 16 and is preferably generally shaped as a shoe insole for insertion into a shoe (not specifically illustrated) or the like.

Magnet 12 is a flexible permanent magnet having a planar North pole segment 12a and a planar South pole segment 12b. As best shown in FIG. 2, the magnet 12 could be elongated into a magnetic strip 22, which thus cooperates with a plurality of consecutive sensor locations, so as to providing a cost savings by easing the manufacture of the apparatus of the present invention.

In the preferred embodiment, Hall-effect transducer 14 is a commercially available, linear-output transducer, such as Sprague P/N UGN3503U. As is known, Hall-effect transducers of this type accurately track extremely small variations in magnetic flux density, or magnetic field strength.

Internally, the transducer 14 has a Hall sensing element, a linear amplifier and an "emitter-follower"-type output stage. Hall-effect transducer 14 has three leads, one for $V_s$ (the supply voltage), one for Grd (ground) and one for $V_o$ (the output voltage). When there is no magnetic field present, the transducer output voltage is referred to as the null voltage, and is approximately one-half of $V_s$.

The transducer output voltage preferably has a positive value when a South pole magnetic field is present. Conversely, the transducer output voltage is negative when a North pole magnetic field is present. Of course, the output voltage of the transducer can be offset such that the transducer output simply decreases, although remaining positive, when a North pole magnetic field is present. Wire harness 28 supplies $V_s$ and Grd to the transducers 14 and communicates the transducer output $V_o$ to a computer (not specifically illustrated) for processing.

As shown in FIG. 1, deformable square 16 has a first side 18 and a second side 20. Deformable square 16 is made of a commercially available elastomeric material such as Neoprene, silicone or polyurethane. These materials are generally listed in the order of decreasing stiffness, K, (i.e. increasing compliance, C), where $C=1/K$. In the preferred embodiment, deformable square 16 has a thickness ranging from about 0.05" to about 0.375" and a compliance for a maximum value of load ranging from about 0.01" to about 0.250".

As best shown in FIG. 2, an array of sensors 10 is preferably disposed around deformable pad 26, thereby permitting the measurement of forces exerted on the load bearing portions of the foot. FIG. 2 illustrates a possible placement scheme for a 48-sensor array.

With continuing reference to FIG. 1, magnet 12 is affixed to the first side 18 of deformable square 16 utilizing any of the known potting compounds compatible with the magnet and deformable square 16. Hall-effect transducer 14 is affixed to the second side 20 of deformable square 16 in a similar manner so that the transducer 14 is generally aligned with the center of the South pole segment 12b, where the magnetic field strength is a maximum. In addition, the transducer 14 should be aligned generally orthogonally to the magnet 12, as is recommended by the manufacturer. The magnet 12, however, could be affixed to the second side 20 and the Hall-effect transducer 14 could be affixed to the first side 18.

Figure 3A:
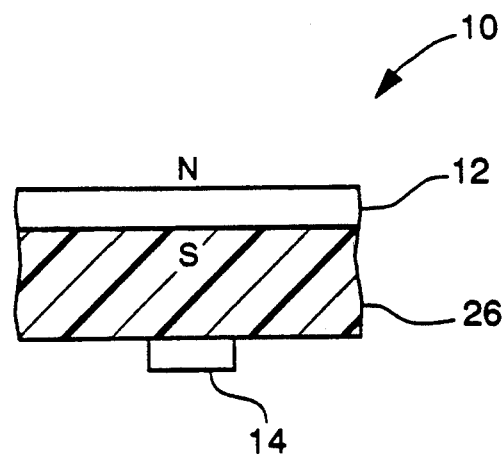
FIGS. 3a-3b are a time sequence illustrating the application of a normal force to the sensor shown in FIG. 1.
Figure 3B:
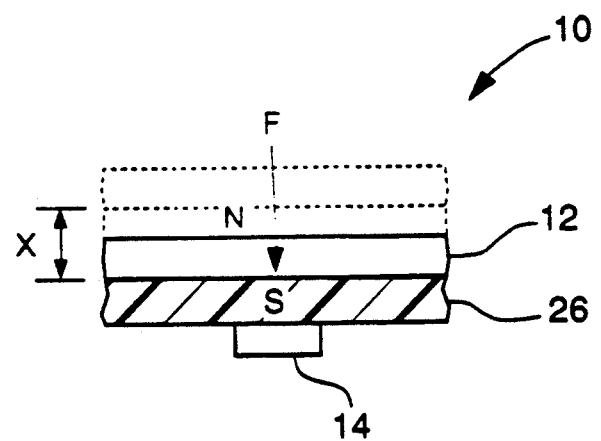

As best shown in FIG. 3a and FIG. 3b, as the force "F" to be measured is exerted on the sensor 10, the deformable pad 26 deforms a distance "X", bringing magnet 12 and Hall-effect transducer 14 into close proximity. Hall-effect transducer 14 is then able to sense the magnet field strength associated with the South pole segment 12b of magnet 12 and output a corresponding voltage signal. Thus, $$F_{NORMAL} = K \cdot X = \left(\frac{1}{C}\right) \cdot X$$

In this embodiment, the magnitude of the Hall-effect transducer 14 output is directly proportional to the magnitude of the force exerted on the sensor 10. As the magnitude of the force increases, the magnet 12 and Hall-effect transducer 14 are brought closer together, thereby exposing the transducer 14 to a stronger magnetic field.

Figure 4:
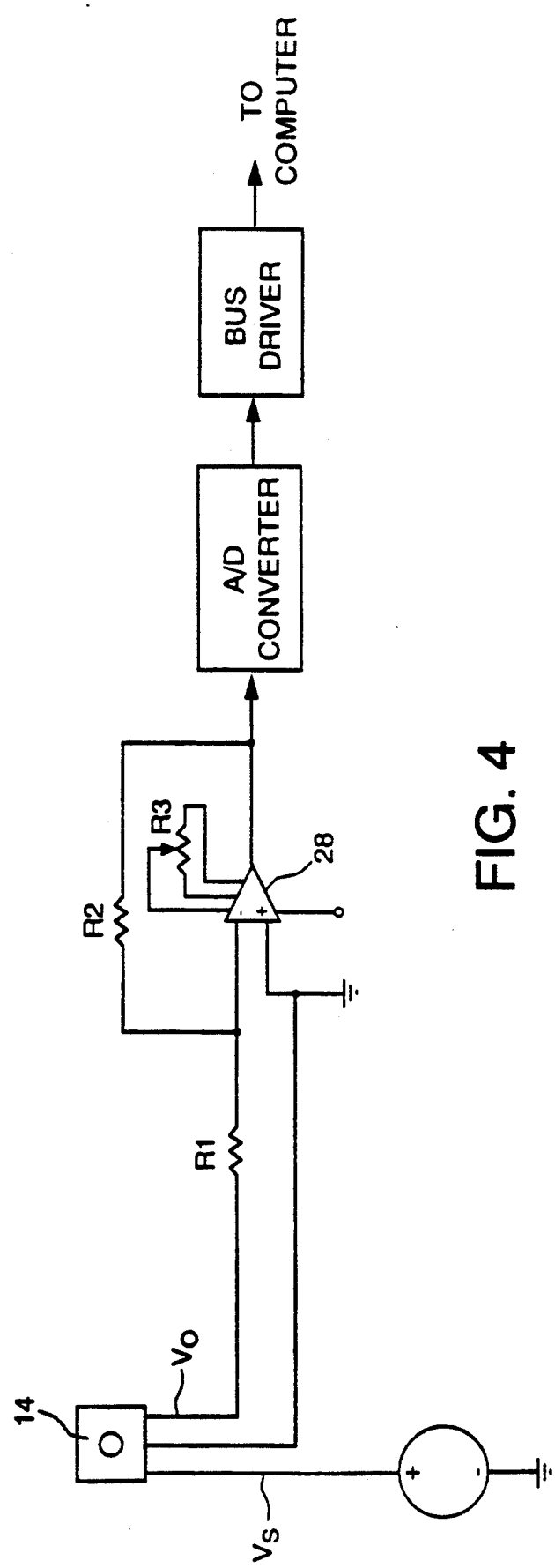
FIG. 4 is a schematic representation of the signal conditioning and computer interface circuitry for use with various sensors of the present invention.

The output of the Hall-effect transducer 14 is preferably "conditioned" by the signal conditioning and computer interface circuitry, as shown in FIG. 4, prior to processing by the computer. An inverting operational amplifier (Op-amp) 28 permits the magnitude of the transducer 14 output ($V_o$), a known low-level voltage, to be boosted to several volts in magnitude.

The boosted signal is then converted from an analog signal to a digital signal, utilizing an analog-to-digital (A/D) conversion integrated circuit, such as the ADC0804, manufactured by National Semiconductor. A bus driver, such as the 74LS244, controls the interface of the data with the data bus of the computer, which then processes the information. The block diagram shown, of course, represents one method of signal conditioning and computer interface and that many other circuits could perform substantially the same function.

Shear Force Sensing

Figure 5:
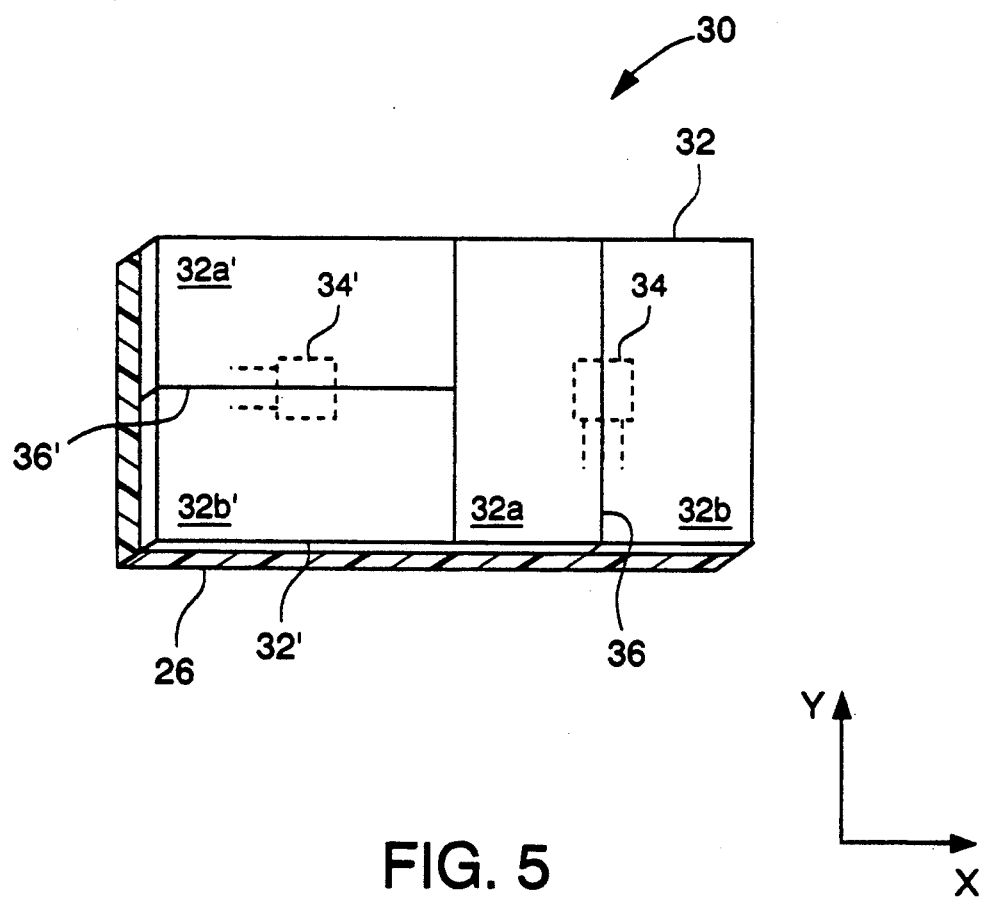
FIG. 5 is a perspective view of the sensor embodiment for measuring the magnitude and direction of two-dimensional shear forces in accordance with the present invention.

Referring now to FIG. 5, the second embodiment of the load sensing apparatus of the present invention is shown. This embodiment is useful for measuring the magnitude and direction of two-dimensional shear forces and comprises the deformable pad 26 and a plurality of sensors 30.

Sensor 30 has two magnets 32 and 32' and two Hall-effect transducers 34 and 34' affixed to opposite sides of the deformable pad 26. Unless otherwise noted herein below, strip magnet 32 is essentially identical to strip magnet 32', and Hall-effect transducer 34 is essentially identical to Hall-effect transducer 34'. As in the previous embodiments, an array of sensors 30 is disposed around deformable pad 26, thereby permitting the measurement of the magnitude and direction of the shear forces exerted on the load bearing portions of the foot.

Strip magnet 32 is preferably a flexible permanent magnet having an imprint of alternating North pole 32a and South pole 32b segments disposed longitudinally therewithin. A magnetic "null point" (i.e. where the magnetic field strength is negligible) exists at the juncture 36 between consecutive North pole 32a and South pole 32b segments and is shown generally by reference numeral 36. In this embodiment, the Hall-effect transducers 34 and 34' are aligned orthogonally with the null point 36 and 36', respectively.

As shown in FIG. 5, to permit measurement of shear forces exerted along the X-axis in the X-Y plane, strip magnet 32 is oriented so that North pole segment 32a and South pole segment 32b are generally perpendicular to the X-axis. Similarly, to permit measurement of shear forces exerted along the Y-axis, magnet 32' is oriented so that North pole segment 32a' and South pole segment 32b' are generally perpendicular to Y-axis displacement. In other words, magnets 32 and 32' are oriented so that their respective pole segments are generally perpendicular. Of course, magnet 32 could be oriented to measure Y-axis shear forces and magnet 32' could be oriented to measure X-axis shear forces.

Figure 6:
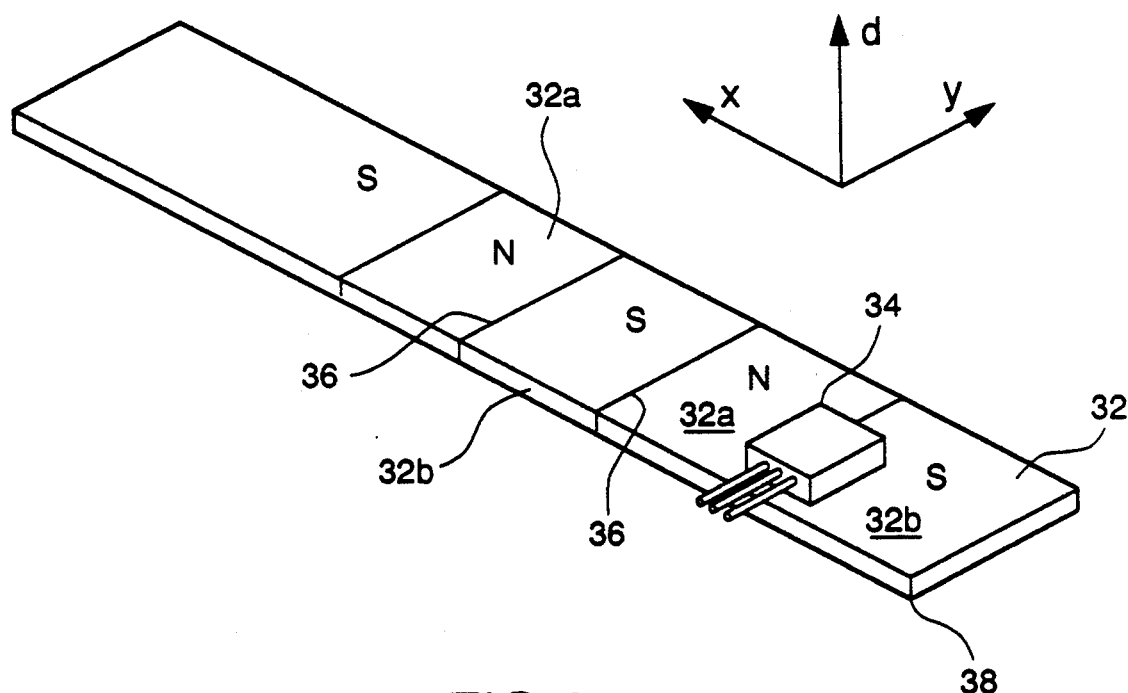
FIG. 6 is an illustration of the test fixture utilized to measure the Hall-effect response to the sinusoidal magnetic field of the strip magnet having an imprint of alternating North and South pole segments in accordance with the present invention.

The alternating North and South pole segment arrangement of the strip magnet 32 creates a generally sinusoidal magnetic field. To determine the characteristics of the magnetic field, a test fixture comprising the strip magnet 32 and the Hall-effect transducer 34 can be set-up as shown in FIG. 6. The coordinate position (x=0, d=0, y=0) represents the lower right corner of the strip magnet 32 indicated by reference numeral 38. Generally, the Hall-effect transducer 34 is positioned over the strip magnet and is moved therealong in the positive X-direction, so as to cross consecutive pole segments.

Figure 7:
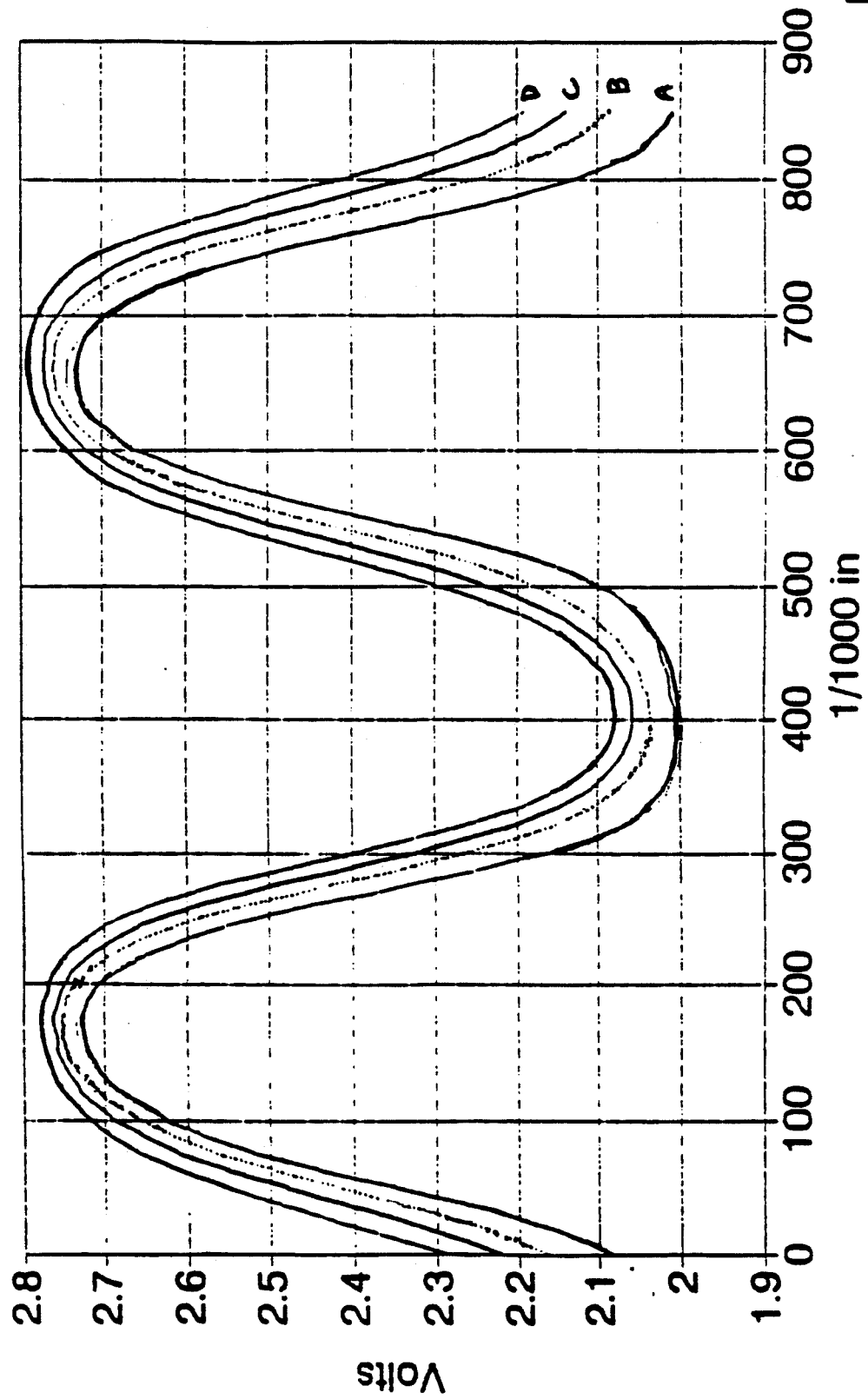
FIG. 7 is a graphical representation of the measured Hall-effect response to the sinusoidal magnetic field taken at various points along the strip magnet, utilizing the test fixture shown in FIG. 6.

Referring now to FIG. 7, the generally sinusoidal field of strip magnet 32 measured by the Hall-effect transducer 34 when moved along the magnet 32 in three different paths is shown. For each plot, the Hall-effect transducer 34 was positioned at distance d=0.035 inches above the strip magnet 32 and moved along the X-axis. Plot A represents the response to the field measured for y=0.0 inches, plot B represents the response to the field measured for y=0.100 inches, plot C represents the response to the field measured for y=0.125 inches and plot D represents the response to the field measure y=0.15 inches.

With continuing reference to FIG. 6 and FIG. 7, when the transducer 34 is generally at the center of a South pole 32b segment, the magnetic field strength has a maximum "positive" value and the transducer output voltage has a maximum positive value. As the transducer 34 is moved from the center toward the null point, the magnetic field strength becomes negligible and the transducer output decreases to the null voltage. The magnetic field strength then increases to a maximum "negative" value and the transducer output voltage further decreases to a minimum positive value as the transducer 34 is moved from the null point 36 toward the center of a North pole segment 32a.

As best shown in FIG. 7, the magnetic field strength varies within pole segments as the Y-position changes. This characteristic is manifested as variations in the shape of the peaks and valleys of the transducer output voltage. This attribute aids in the determination of the magnitude and direction of a shear force which, unlike normal forces, can displace the transducer 34 in the Y-direction within pole segments.

Figure 8A:
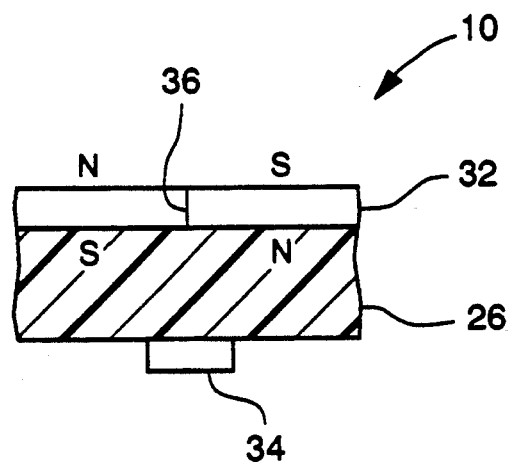
FIGS. 8a-8b are a time sequence illustrating the application of a shear force to a sensor and the associated off-center aspect of shear force sensing, in accordance with the present invention.
Figure 8B:
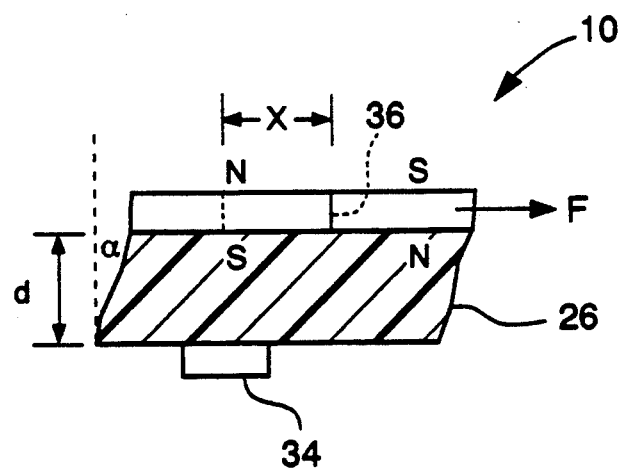

Referring now to FIG. 8a and FIG. 8b, shear force sensing generally involves an off-center aspect of magnetic field sensing. As a shear force "F" to be measured is exerted on the sensor 30, the deformable pad 26 deforms, the magnet is displaced a distance "X" in relation to the Hall-effect transducer. Thus, $$K = \left(\frac{F}{d\tan\gamma}\right) = \left(\frac{F}{dy}\right) = \frac{F}{X}$$

where "X" produces the $V_o$ from the transducer.

If the shear force is exerted only in a positive X-plane direction (no Y-plane component), the North pole segment 32a is displaced toward the Hall-effect transducer 34 so that the transducer is no longer aligned with the null point 36. The transducer 34 then senses the increased magnetic field strength and outputs a corresponding voltage signal. The transducer 34' remains generally aligned with the null point 36' and therefore is exposed only to a negligible magnetic field.

If the shear force is exerted only in a positive Y-plane direction (no X-plane component), the South pole segment 32b' is displaced toward the Hall-effect transducer 34' so that the transducer is no longer aligned with the null point 36'. The transducer 34' then senses the increased magnetic field strength and outputs a corresponding voltage signal. Transducer 34 remains generally aligned with the null point 36, exposed only to a negligible magnetic field.

A third possibility is a shear force having both X- and Y-plane components (i.e. a force exerted at some angle to the X and Y planes). For a shear force exerted at a 45° angle, for example, North pole segment 32a and South pole segment 32b' are displaced toward the Hall-effect transducers 34 and 34', respectively, and are no longer aligned with their respective null points. Both transducers 34 and 34' then sense an increased magnetic field strength and output a corresponding voltage signal.

Figure 9:
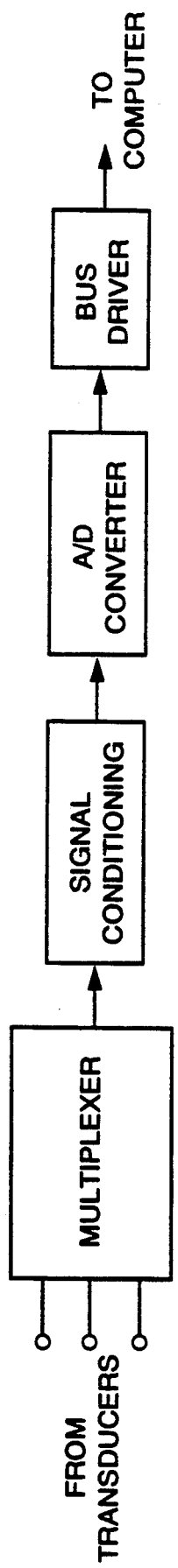
FIG. 9 is a block diagram of the signal conditioning and computer interface circuitry for use with sensor embodiments of the present invention having more than one transducer.

Referring now to FIG. 9, there is shown the signal conditioning and computer interface circuitry for conditioning the transducer output voltage signals prior to processing by the computer. As described in greater detail above, the magnitude of the transducer voltage signals are directly proportional to the magnitude of the force exerted on the pad and sensor. Based on the output of the transducers 34 and 34', the computer can determine how the transducers and magnets were displaced and, using commonly known trigonometric techniques, determine the magnitude and direction of the resultant shear forces exerted on the foot.

As illustrated in FIG. 9, a multiplexer, such as a commercially available CD4067, is utilized since the sensor 30 has more than one Hall-effect transducer. The signal conditioning block of FIG. 9 preferably utilizes the inverting Op-amp circuitry previously shown in greater detail in FIG. 4.

Normal and Shear Force Sensing

Figure 10:
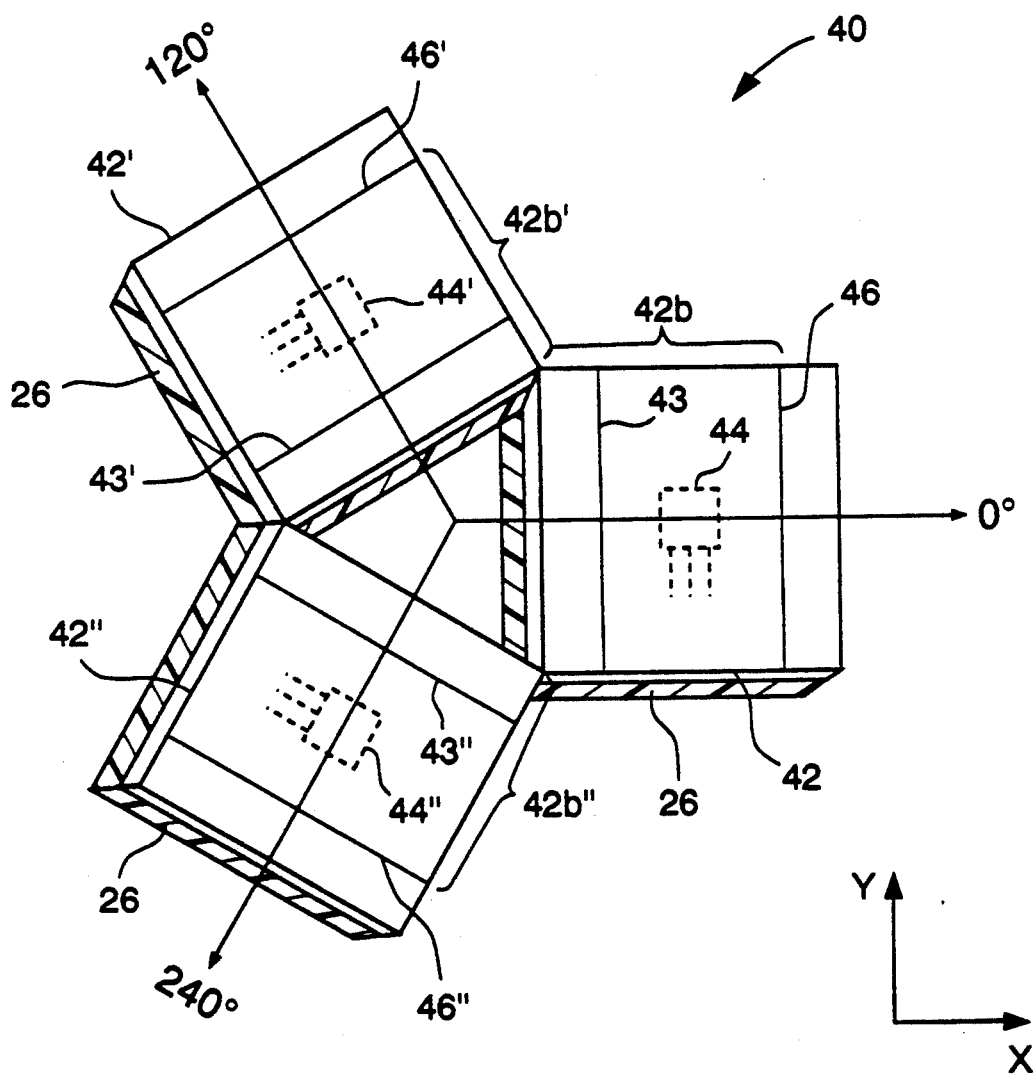
FIG. 10 is a perspective view of a sensor embodiment for measuring normal forces and the magnitude and direction of two-dimensional shear forces, in accordance with the present invention.

Referring now to FIG. 10, another embodiment of the present invention is shown, useful for measuring the magnitude and direction of normal forces and two-dimensional shear forces. This embodiment utilizes an array of sensors 40, wherein each sensor 40 has three substantially similar strip magnets 42, 42' and 42" and three substantially similar Hall-effect transducers 44, 44' and 44", affixed to opposite sides of the deformable pad 26. In this embodiment, the strip magnets 42, 42' and 42" are substantially similar to the strip magnets 32 and 32' discussed above, having alternating North and South pole segments.

As illustrated in FIG. 10, the Hall-effect transducers 44, 44' and 44" are each preferably aligned orthogonally with the magnets 42, 42' and 42", respectively, between a peak South pole 43 (i.e. the center of the South pole segment 42b) and an adjacent null point. Thus, transducer 44 is positioned generally equidistant between the peak South pole 43 and the null point 46. Similarly, transducer 44' is positioned generally equidistant between the peak South pole 43' and the null point 46' and transducer 44" is positioned generally equidistant between the peak South pole 43" and the null point 46".

In the preferred embodiment, each magnet is disposed generally 120° from the other two magnets, to allow for a more compact sensor design. The geometry of this arrangement can also reduces the complexity of the vector mathematics involved in the processing of the output. Of course, other geometries could be utilized, but with increased computation costs.

With continuing reference to FIG. 10, as a normal force is exerted on the sensor 40, each magnet is displaced toward a transducer, which senses the increased flux density and outputs a corresponding signal. As the shear forces to be measured are exerted on the sensor 40, the pad 26 deforms, bringing the Hall-effect transducers 44, 44' and 44" in close proximity to either a peak South pole segment 43, 43' and 43" or a null point 46, 46' and 46", depending on the direction of the shear force. Thus, for a shear force exerted in the direction of the X-axis, the transducer 44 would be proximate the peak South pole 43 and the transducers 44' and 44" would be proximate the null points 46' and 46", respectively. After being conditioned, the corresponding transducer voltage signals are then processed by the computer, as previously described.

Figure 11:
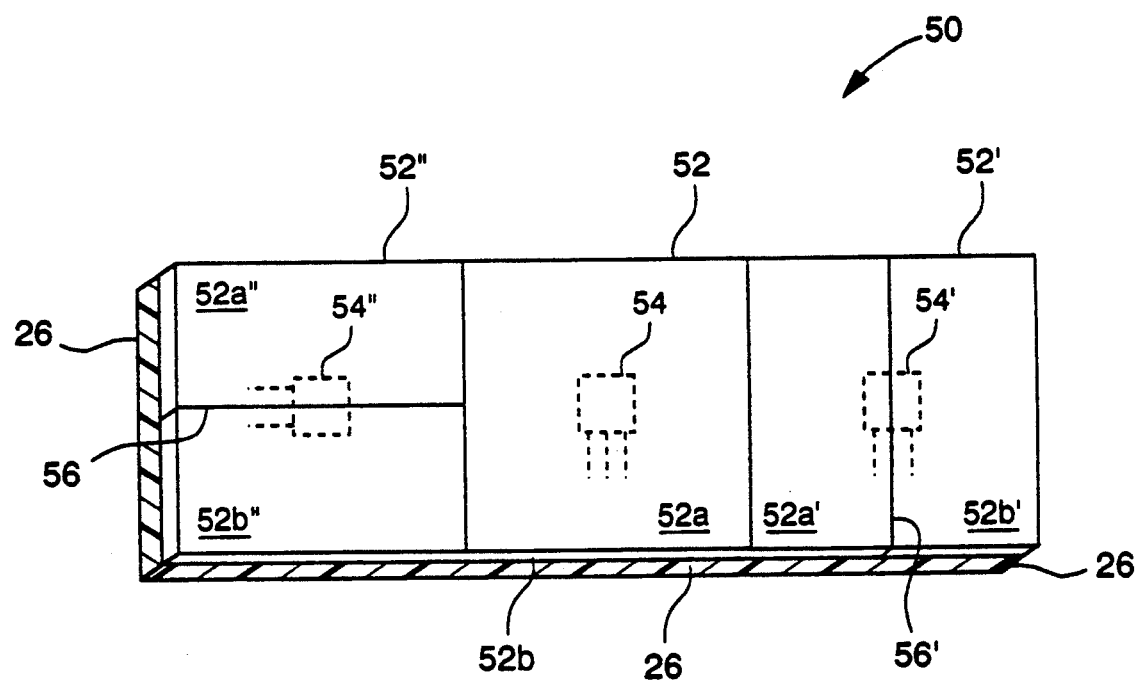
FIG. 11 is a perspective view of an additional sensor embodiment for measuring normal forces and the magnitude and direction of two-dimensional shear forces, in accordance with the present invention.

Turning now to FIG. 11, an additional embodiment of the load and displacement sensing apparatus of the present invention is shown. This embodiment is also useful for measuring the normal forces and the magnitude and direction of two-dimensional shear forces and associated displacements.

In this preferred embodiment, sensor 50 has three magnets 52, 52' and 52" and three Hall-effect transducers 54, 54' and 54" affixed to opposite sides of the deformable pad 26. As in the previous embodiments, an array of sensors 50 is disposed around deformable pad 26, thereby permitting the measurement of the normal and shear forces exerted on the load bearing portions of the foot or other body.

As in the first embodiment, magnet 52 is a flexible permanent magnet having a planar North pole segment 52a and a planar South pole segment 52b. Similarly, strip magnets 52' and 52" are flexible permanent magnets, but have alternating North pole 52a', 52a" and South pole 52b', 52b" segments imprinted longitudinally thereon. Strip magnets 52' and 52", therefore, also have magnetic null points 56' and 56" at the juncture between consecutive North and South pole segments. For the best results, the Hall-effect transducer 54 should be aligned orthogonally with the center of the planar North pole segment 52a and the transducers 54' and 54" should be aligned orthogonally with the null points 56 and 56', respectively.

As shown in FIG. 11, in the preferred embodiment, strip magnet 52' is oriented so that North pole segment 52a' and South pole segments 52b' are generally perpendicular to the X-axis, and strip magnet 52" is oriented so that North pole segment 52a" and South pole segment 52b" are generally perpendicular to Y-axis displacement. As previously described, this orientation permits transducer 54' to measure shear forces and displacements along X-axis and transducer 54" to permit measure shear forces and displacements exerted along the Y-axis.

When a normal force is exerted on the sensor 50, the transducer 54' and 54" are brought in close proximity to the magnets 52' and 52", but remain generally aligned with the null points 56' and 56". Transducer 54 and magnet 52, however, are displaced toward each other so that magnet 52 senses the increased magnet flux density associated with the South pole segment 52b.

With continuing reference to FIG. 11, for a shear force exerted on the sensor 50, transducers 54' and 54" and the null points 56' and 56" are moved in relation to each other, as described in greater detail above, although there is no measurable change in magnetic field strength. Any transducer output signals are conditioned by the signal conditioning and computer interface circuitry shown in FIG. 9. Based on the transducer output, the computer can determine how the transducers and magnets were displaced and, using commonly known trigonometric techniques, determine the magnitude and direction of normal and shear forces exerted on the foot or other body.

Figure 12:
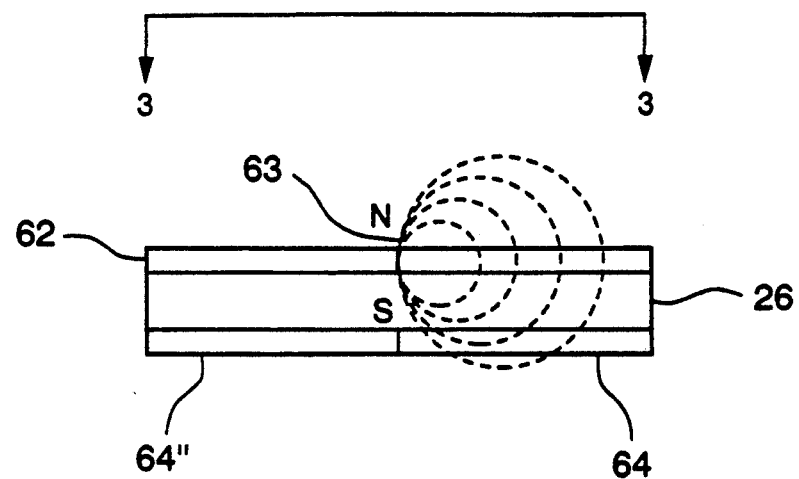
FIG. 12 is a side view of an embodiment utilizing a point magnetization and a plurality of Hall-effect transducers to measure normal forces and the magnitude and direction of two-dimensional shear forces, in accordance with the present invention.
Figure 13:
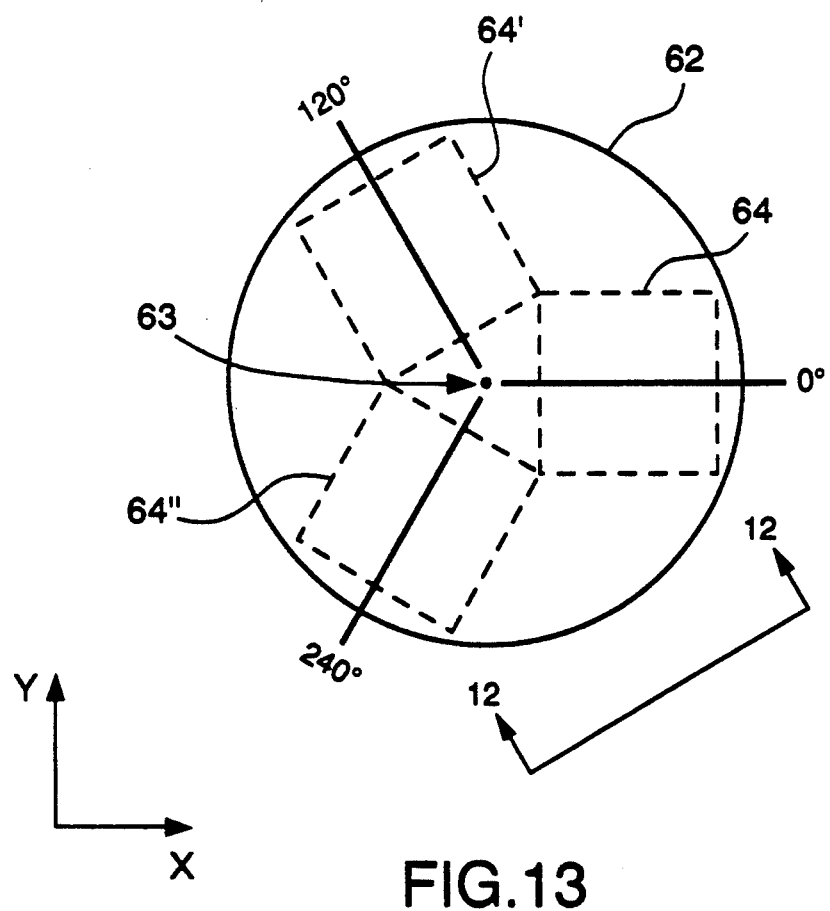
FIG. 13 is a plan view of the embodiment shown in FIG. 12 with the transducers shown in phantom representation.

Referring now to FIG. 12 and FIG. 13, another embodiment for measuring normal and shear forces is shown. In this preferred embodiment, sensor 60 has a single magnet 62 and three Hall-effect transducers 64, 64' and 64" affixed to opposite sides of the deformable pad 26. As in the previous embodiments, an array of the sensors 60 is disposed around a deformable pad 26, thereby permitting the measurement of the normal and shear forces exerted on the load bearing portions of the foot or other body.

As illustrated in FIG. 12 and FIG. 13, the magnet 62 is preferably a flexible permanent magnet having a single point magnetization 63 generally at the center of the magnet, with North and South poles on opposite sides of the magnet. A portion of the flux liens for such a point magnetization are shown in FIG. 12. For the best results, the Hall-effect transducers 64, 64' and 64" are aligned orthogonally with the magnet 62, each transducer being disposed generally 120° from each other.

When a normal force is exerted on the sensor 60, the transducers 64, 64' and 64" are brought in close proximity to the magnet 62. The transducers sense the increased magnetic flux density and output corresponding signals. As a shear force is exerted on the sensor 60, the magnet 62 is moved in relation to the transducers 64, 64' and 64". Thus, for a shear force exerted along the "X" axis, the point magnetization 63 is displaced toward the transducer 64 and away from the transducers 64' and 64". Transducer 64 senses an increases in the magnetic flux density and transducer 64' and 64" generally sense a decrease in the magnetic flux density. The transducer output signals are conditioned by the signal conditioning and computer interface circuitry shown in FIG. 9. Based on the transducer output, the computer can determine how the transducers and magnets were displaced and, using commonly known trigonometric techniques, determine the magnitude and direction of normal or shear forces exerted on the foot or other body.

Normal with Tilt Compensation and Shear Force Sensing

An additional embodiment is useful for measuring normal forces and the magnitude and direction of two-dimensional shear forces and the displacements associated therewith, but also allows for tilt compensation in determining the magnitude of the normal forces.

In the preferred embodiment, the sensor has five flexible permanent magnets that cooperate with five Hall-effect transducers. The magnets and the transducer are affixed to opposite sides of the deformable pad. As in the previous embodiments, an array of sensors is disposed around deformable pad, thereby permitting the measurement of the normal and shear forces exerted on the load bearing portions of the foot or other body.

Three magnets have a planar North pole segment and a planar South pole segment and cooperate with three Hall-effect transducers, respectively. These transducers are preferably aligned orthogonally with the magnets. The other two magnets are strip magnets and have alternating North pole and South pole segments, respectively, disposed longitudinally therewithin and cooperate with transducers.

The strip magnets also have magnetic null points located generally at the juncture between consecutive North and South pole segments. For the best results, the Hall-effect transducers should be aligned orthogonally with null points.

The magnets are useful for measuring shear forces and displacements and are preferably oriented similar to the magnets 32 and 32' shown in FIG. 5. This orientation permits transducer to measure shear forces along the X-axis and transducer to permit measure shear forces exerted along the Y-axis. If a shear force is exerted on the sensor, the transducers move in relation to the null points as described in greater detail above, and sense the change in the magnetic field strength.

The magnets are most useful for measuring normal forces and displacements and are preferably disposed around the magnets. In addition to providing a compact sensor design, this orientation permits tilt compensation for more accurate measurement of normal forces than would be possible with the embodiment shown in FIG. 1, as described herein below.

A normal force is applied to the foot at a point where a sensor is located, the magnitude of the normal force is generally exerted on the transducers and magnets equally. The resulting displacement of each transducer and the corresponding movement toward each other as the pad deforms will also generally be equal, due to the symmetry of the orientation of the magnets. During processing, the computer can therefore determine the nature of the force based on this similarity of the output of each transducer.

If, however, a force is exerted on the foot at a point toward the edge of the sensor, the sensor is "tilted" and the displacement of transducer and magnet toward each other will generally be greater than the displacements of transducers and magnets. Accordingly, the change in magnetic flux density sensed by transducer, and the resulting transducer output, will be greater.

As described in greater detail above, the transducer output signals are conditioned by the signal conditioning and computer interface circuitry shown in FIG. 4 prior to processing by the computer. Based on the dissimilarity of the output signals of transducers resulting from the tilt, it is therefore possible to more accurately measure the force and determine its point of application to the foot.

Various other uses of the sensors described herein above will be readily appreciated by one of ordinary skill in the art. For example, a finger-operated device employing one of the sensors previously described (e.g. sensor 50 shown in FIG. 11) could be incorporated into a computer keyboard and used to control cursor position.

As the user "pushes" on the keyboard sensor with his finger in a certain direction, shear forces would be exerted on the sensor 50. Theses shear forces are then sensed and processed, resulting in cursor movement in the direction of the "push". Cursor displacement on the computer monitor is directly proportional to the magnitude of the force. The further ability of sensor 50 to sense a normal force would allow such a device to operate as the conventional computer "mouse" operates (i.e. "clicking and dragging" equates to exerting a normal force and exerting shear forces).

It is understood, of course, that while the forms of the invention herein shown and described constitute the preferred embodiments of the invention, they are not intended to illustrate all possible forms thereof. It will also be understood that the words used are words of description rather than limitation, and that various changes may be made without departing from the spirit and scope of the invention disclosed.

What is claimed is:

1. An apparatus for load and displacement sensing adapted for measuring the magnitude and direction and two-dimensional shear forces exerted upon the load bearing portions of a body, the apparatus comprising:
   a deformable pad having a first and second side, and
   a plurality of sensors, each sensor having three magnets affixed to one side of said deformable pad and three transducers for sensing the magnetic field strength affixed to the other side of said deformable pad, each transducer being aligned with one of said magnets and having an output which varies according to the magnitude and direction of said normal and two-dimensional shear forces, said forces moving said magnets in relation to said transducers, said magnets are oriented so that their respective pole segments are disposed 120° from each other.

* * * * *